US011191918B2

(12) United States Patent
Ho et al.

(10) Patent No.: US 11,191,918 B2
(45) Date of Patent: *Dec. 7, 2021

(54) PATIENT INTERFACE ASSEMBLY WITH SELF-ADJUSTING ANCHOR POINTS (71) Applicant: KONINKLIJKE PHILIPS N.V., Eindhoven (NL)

(72) Inventors: Peter Chi Fai Ho, Pittsburgh, PA (US); Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 911 days.

This patent is subject to a terminal disclaimer.

(21) Appl. No.: 15/446,149

(22) Filed: Mar. 1, 2017

(65) Prior Publication Data
US 2017/0173292 A1 Jun. 22, 2017

Related U.S. Application Data (62) Division of application No. 14/239,267, filed as application No. PCT/IB2012/054226 on Aug. 21, 2012, now Pat. No. 9,610,419.

(60) Provisional application No. 61/526,458, filed on Aug. 23, 2011.

(51) Int. Cl.
A61M 16/06 (2006.01)
A61M 16/00 (2006.01)
A61M 16/08 (2006.01)

(52) U.S. Cl.
CPC .... *A61M 16/0683* (2013.01); *A61M 16/0057* (2013.01); *A61M 16/0816* (2013.01); *A61M 2210/0618* (2013.01); *A61M 2210/0625* (2013.01)

(58) Field of Classification Search
CPC . A61M 16/06; A61M 16/0683; A62B 18/084; A62B 9/04; A62B 7/00; A41D 13/11; A41D 13/1161
See application file for complete search history.

(56) References Cited

U.S. PATENT DOCUMENTS 2,912,978 A * 11/1959 Seeler ............ A62B 18/084
128/201.23
3,416,521 A * 12/1968 Hamlin ........... A62B 18/084
128/207.11
3,513,841 A * 5/1970 Seeler ............ A62B 18/084
128/201.23
5,555,569 A * 9/1996 Lane .................. A42B 3/288
128/201.22

(Continued)

FOREIGN PATENT DOCUMENTS

CN 101888869 A 11/2010
CN 101951984 A 1/2011
(Continued)

Primary Examiner — Kathryn E Ditmer
(74) Attorney, Agent, or Firm — Michael W. Haas (57) ABSTRACT A patient interface assembly having an improved support for use in securing a patient interface device to the head of a patient overcomes the shortcomings of conventional headgear. The improved support provides a self-adjusting anchor point situated anterior to the ear of the patient that provides enhanced stability in mounting the patient interface device to the patient.

11 Claims, 5 Drawing Sheets

(56) References Cited

U.S. PATENT DOCUMENTS

| | | | | |
|---|---|---|---|---|
| 6,119,694 A * | 9/2000 | Correa | ............. | A61M 16/0666 |
| | | | | 128/207.13 |
| 7,296,575 B1 | 11/2007 | Radney | | |
| 2003/0111080 A1 * | 6/2003 | Olsen | ............... | A61M 16/0069 |
| | | | | 128/207.11 |
| 2004/0069302 A1 * | 4/2004 | Wilson | ............... | A41D 13/1184 |
| | | | | 128/201.24 |
| 2004/0112377 A1 | 6/2004 | Amarasinghe | | |
| 2005/0103344 A1 | 5/2005 | Cheng | | |
| 2005/0227834 A1 | 10/2005 | Lorelli | | |
| 2006/0090760 A1 * | 5/2006 | Gradon | ............. | A61M 16/0633 |
| | | | | 128/206.27 |
| 2006/0237017 A1 * | 10/2006 | Davidson | ............ | A61M 16/06 |
| | | | | 128/205.25 |
| 2006/0237018 A1 * | 10/2006 | McAuley | ........... | A61M 16/0616 |
| | | | | 128/206.24 |
| 2007/0125385 A1 * | 6/2007 | Ho | ........................ | A61M 16/06 |
| | | | | 128/206.26 |
| 2007/0209663 A1 * | 9/2007 | Marque | ............. | A61M 16/0683 |
| | | | | 128/207.11 |
| 2011/0067704 A1 * | 3/2011 | Kooij | ................ | A61M 16/0666 |
| | | | | 128/207.18 |

FOREIGN PATENT DOCUMENTS

| | | | | |
|---|---|---|---|---|
| EP | 2060294 A1 | 5/2009 | | |
| WO | WO2005032634 A1 | 4/2005 | | |
| WO | WO-2009052560 A1 * | 4/2009 | ........ | A61M 16/0875 |
| WO | WO2009052560 A1 | 4/2009 | | |
| WO | WO2009063402 A1 | 5/2009 | | |
| WO | WO2010073142 A1 | 7/2010 | | |
| WO | WO-2011077254 A2 * | 6/2011 | ........ | A61M 16/0057 |
| WO | WO2011077254 A2 | 6/2011 | | |

* cited by examiner

PATIENT INTERFACE ASSEMBLY WITH SELF-ADJUSTING ANCHOR POINTS

CROSS-REFERENCE TO RELATED APPLICATIONS

This patent application is a Divisional of U.S. patent application Ser. No. 14/239,267, filed Feb. 18, 2014, which claims the priority benefit under 35 U.S.C. § 119(e) of U.S. Provisional Application No. 61/526,458 filed on Aug. 23, 2011, the contents of which are herein incorporated by reference.

BACKGROUND OF THE INVENTION

1. Field of the Invention

The present invention pertains to patient interface assemblies and, in particular, to an improved support for use in securing a patient interface device, such as a mask, to a patient.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome in particular, obstructive sleep apnea (OSA), or congestive heart failure.

Non-invasive ventilation and pressure support therapies involve the placement of a patient interface device including, such as a mask, on the face of a patient. The patient interface device may be, without limitation, a nasal mask that covers the patient's nose, a nasal cushion having nasal prongs that are received within the patient's nares, a nasal/oral mask that covers the nose and mouth, or full face mask that covers the patient's face. The patient interface assembly interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

For patient interface devices, a key engineering challenge is to balance patient comfort against stability of the device. As a patient changes sleeping positions through the course of the night, the mask portions of respiratory patient interface devices may become dislodged, and the seal against the patient may be broken. A dislodged mask portion can be stabilized by the increasing strapping force provided by the headgear, but increased strapping force tends to reduce patient comfort. This design conflict is further complicated by the widely varying facial geometries that a given respiratory patient interface device design needs to accommodate.

SUMMARY OF THE INVENTION

Accordingly, it is an object of the present invention to provide a patient interface assembly having an improved support for use in securing a patient interface device to the head of a patient that overcomes the shortcomings of conventional headgear. The improved support provides a self-adjusting anchor point situated anterior to the ear of the patient that provides enhanced stability in mounting the patient interface to the patient.

Another object of the present invention is to provide an improved support that can be used in supporting a patient interface device on a patient. Such an improved support likewise provides a self-adjusting anchor point anterior to the ear of the patient.

An optional feature provided in the improved support is that in addition to a strap that supports the patient interface device being movable with respect to a plurality of connectors that connect the strap with the headgear, the connectors may optionally be themselves movably disposed on the headgear.

In certain embodiments, the general nature of the invention can be stated as including a patient interface assembly structured to provide a flow of breathing gases to a patient. The patient interface assembly can be generally stated as including a headgear, a patient interface device, and a support. The headgear is structured to extend across at least one of an occipital region and a parietal region of the patient's head. The patient interface assembly is structured to supply a flow of breathing gases to the mouth or the nose or both of a patient. The support extends between the headgear and the patient interface and can be said to include a strap apparatus and a pair of connectors. The strap apparatus can be said to include a pair of flexible strap segments that extend from opposite sides of the patient interface, with each strap segment extending from two location on the patient interface. The pair of connectors are disposed on opposite sides of the headgear. Each strap segment is movably connected with a connector of the pair of connectors.

In certain embodiments, the general nature of the invention can be stated as including a support that is structured to extend between a headgear and a patient interface of a patient interface assembly. The headgear is structured to extend across at least one of an occipital region and a parietal region of a patient's head. The patient interface assembly is structured to supply a flow of breathing gases to the mouth or the nose or both of the patient. The support can be generally stated as including a strap apparatus and a pair of connectors. The strap apparatus can be generally stated as including a pair of flexible strap segments that extend from opposite sides of the patient interface, with each strap segment extending from two location on the patient interface. The pair of connectors are disposed on opposite sides of the headgear. Each strap segment is movably connected with a connector of the pair of connectors.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
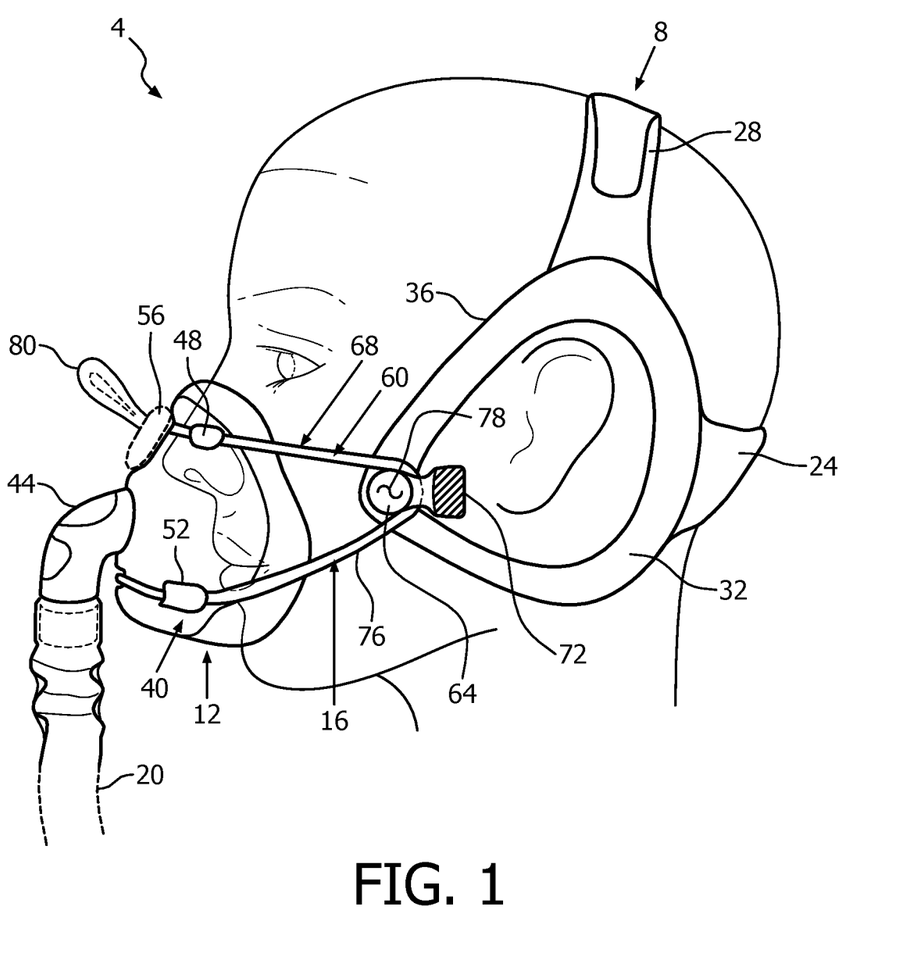
FIG. 1 is a side elevational view of a patient interface assembly in accordance with a first embodiment of the invention, it being understood that the other side of the patient interface assembly is a mirror image of what is depicted in FIG. 1.

A patient interface assembly 4 in accordance with a first embodiment of the present invention is depicted in FIG. 1 as being situated on a patient. As suggested above, the other side of patient interface assembly 4 is a mirror image of what is depicted in FIG. 1 and, thus, is not expressly shown herein for purposes of simplicity of disclosure. The alternative embodiments of patient interface assembly 4 are likewise shown in side elevational views, it being understood that the non-depicted sides are mirror images thereof.

As can be seen in FIG. 1, patient interface assembly 4 can be said to include a headgear 8, a patient interface device 12, and a support 16 that extends between headgear 8 and patient interface device 12. As is understood in the relevant art, patient interface assembly 4 is configured to provide a flow of breathing gases to a patient.

More particularly, patient interface device 12 is in fluid communication with the patient's mouth or nose or both in order to provide the flow of breathing gases to the patient. Patient interface device 12 is connectable with a supply line 20 that provides the flow of breathing gases. It is noted that patient interface device 12 shown in FIG. 1 and the other patient interfaces devices shown in FIGS. 2, 4, and 5 that are described below are depicted in a schematic and exemplary fashion since virtually any type of patient interface device can be employed in conjunction with the improved breathing apparatus 4 and the improved support 16. The present invention contemplates that patient interface device can be any devices that communicates a flow of gas with an airway of a user, such as a nasal mask, nasal oral mask, nasal pillows, nasal cannular, or a full or total mask that covers the face.

Exemplary headgear 8 includes an occipital element 24 that extends across the occipital region of the patient, a parietal element 28 that extends across the parietal region of the patient, and a pair of temporal elements 32 that each extend generally between occipital element 24 and parietal element 28. Headgear 8 further includes a pair of anterior struts 36 that extend in an anterior direction from temporal elements 32 and which, when situated on a patient, extend across a region anterior to the ears. It is noted, however, that many features of headgear 8 of FIG. 1 and the headgear depicted in FIGS. 2-5 are largely of an exemplary nature except as expressly pointed out herein. In this regard, it is noted that headgear 8 can be of other configurations without departing from the present concept.

Patient interface device 12 can be said to include a mask 40 having a fluid connection 44 for connection with supply line 20. Patient interface device 12 includes a pair of upper braces 48 situated on mask 40 and a pair of lower braces 52 likewise situated on mask 40. Upper and lower braces 48 and 52 are in the exemplary form of tunnels and are situated generally in the upper and lower regions of mask 40, respectively, when mask 40 is situated on the patient. Upper braces 48 are spaced from lower braces 52 in order to cooperate in a self-adjusting manner with support 16, as will be set forth in greater detail below. Patient interface device 12 further includes an adjustment element 56 that is situated generally between upper braces 48 and which will be described in greater detail below.

The improved support 16 can be said to include a strap apparatus 60 and a pair of connectors 64. Each connector 64 is affixed to one of the pair of anterior struts 36 and enables connection of strap apparatus 60 with headgear 8. Strap apparatus 60 includes an individual, i.e., unitary and single, strap member 68 and a pair of tabs 72 that are connected with strap member 68. While strap member 68 is, in the depicted exemplary embodiment, an individual, i.e., continuous strap, it is noted that for purposes of the disclosure herein strap member 68 can be said to include a pair of strap segments 76 that extend from the opposite sides of mask 40 and are connect with connectors 64.

More particularly, it can be seen from FIG. 1 that each of the pair of strap segments 76 can be said to extend from the lower midpoint of mask 40, through one of the pair of lower braces 52, and extend in an posterior direction therefrom, extending about connector 64, and then extend in an anterior direction, extend through one of the pair of upper braces 48, and connects with a portion of a tension loop 80 of the strap member 68 that is formed via cooperation with adjustment element 56. That is, the user can apply a force to tension loop 80, which serves as an adjustment element, to increase the tension within strap member 68, and adjustment element 56 retains tension loop 80 in the desired position to retain the resultant tension within strap member 68. Adjustment element 56 can be in any of a wide variety of forms that may include engagement structures which pinch strap member 68 to retain it in position, or can employ other structures that are well known in the relevant art.

Tabs 72 are each situated on strap segments 76 and can be grasped by the patient and pulled rearward, i.e., in a posterior direction, during initial installation of mask 40 on the face of the patient in order to cause strap members 68 to be pulled, perhaps at least partially elastically, and to extend behind and movably engage connectors 64. While tabs 72 are depicted in FIG. 1 as physically contacting connectors 64, such depiction is intended merely for purposes of illustration, it being understood that tabs 72 might not necessarily be disposed so closely to connectors 64 once the tension in strap member 68 reaches a state of equilibrium.

In this regard, it is expressly noted that strap segments 76 extend about a posterior surface of connectors 64 and are movable with respect thereto in order to enable the tension within the upper and lower portions of strap segments 76 to reach an equilibrium. That is, when the tension in strap member 68 is adjusted by the patient by either pulling or releasing tension loop 80, or by adjusting patient interface device 12, the tension in the upper and lower portions of strap segments 76 may at least initially be unequal. However, since each strap segment 76 is movably disposed on its corresponding connector 64, i.e., is movable with respect thereto, the various tensions within the upper and lower portions of each strap segment 76 will eventually equalize by movement of strap segments 76 along connectors 64. This is desirable since it equalizes the compression forces of mask 40 at its upper and lower ends where it connects with the patient's face, which desirably enhances comfort and fit.

Also notably, the connection of each strap segment 76 with the corresponding connector 64 provides an anchor point 78 that is situated anterior to the ear of the patient and that advantageously is self-adjusting. Such self-adjustment exists not only in terms of tension within strap segments 76, but it also exists in respect of the positioning of mask 40 on any of a variety of patient having different facial structures. That is, if the patient's nose and mouth were positioned relatively higher on the face than is depicted in FIG. 1, strap segments 76 would still movably extend about connectors 64 to provide self-adjusting anchor points 78 that are situated anterior to the ears. Thus, regardless of the specific position and orientation of mask 40, the tension within the upper and lower portions of each strap segment 76 will eventually become equalized due to the movable connection between strap segments 76 and connectors 64.

Advantageously, therefore, it can be seen that the self-adjusting anchor points 78 that are provided by support 16 to breathing apparatus 4 enable improved comfort for the patient due to the ability of mask 40 to be mounted to the patient irrespective of the specific facial configuration of the patient since the self-adjusting anchor points 78 facilitate the achievement of equilibrium of tension in the upper and lower portions of each strap segment 76. This advantageously promotes the secure connection between mask 40 and the patient and further promotes comfort for the patient.

Moreover, it can be seen that since strap member 68 is an individual strap element or cord element that is flexible and that may be at least partially elastic, tension between strap segments 76 situated at opposite sides of mask 40 likewise reaches an equilibrium, which avoids pulling of mask 40 to one side or the other of the patient's face. In this regard, it can be seen that strap member 68 is not only movably disposed on connectors 64 but also is movably situated within upper braces 48 and lower braces 52. Despite headgear 8 being relatively rigid, patient interface device 12 can be comfortably and reliably retained on the patient through the use of support 16 with its self-adjusting anchor points 78 situated anterior to the ears of the patient.

Figure 2:
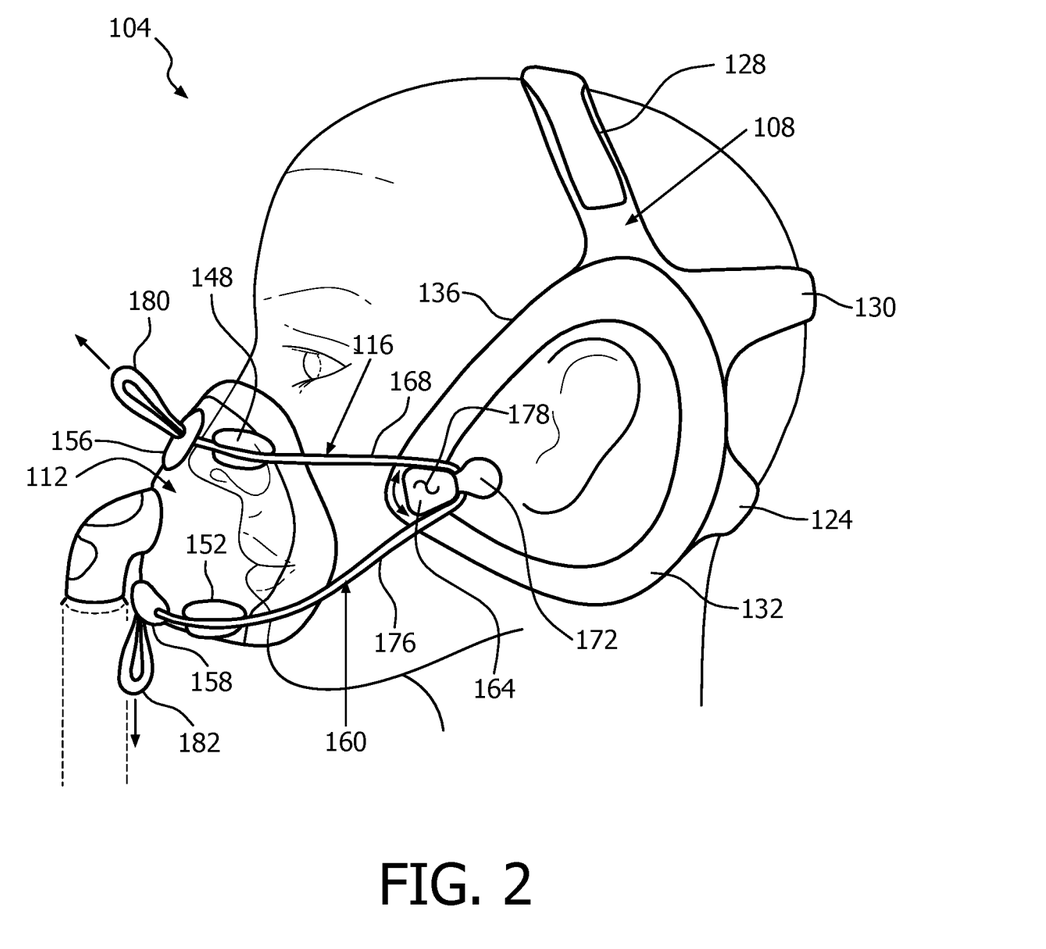
FIG. 2 is a side elevational view of a patient interface assembly in accordance with a second embodiment of the present invention.

An improved patient interface assembly 104 in accordance with a second embodiment of the present invention is depicted generally in FIG. 2. While patient interface assembly 104 is similar to patient interface assembly 4 in many respects, the two nevertheless have some meaningful differences. For example, headgear 108 includes an occipital element 124 and a parietal element 128, but additionally includes an intermediate element 130 situated between occipital and parietal elements 124 and 128. This is a further demonstration that virtually any type of headgear can be advantageously employed in breathing apparatus 4, 104, etc.

Figure 3:
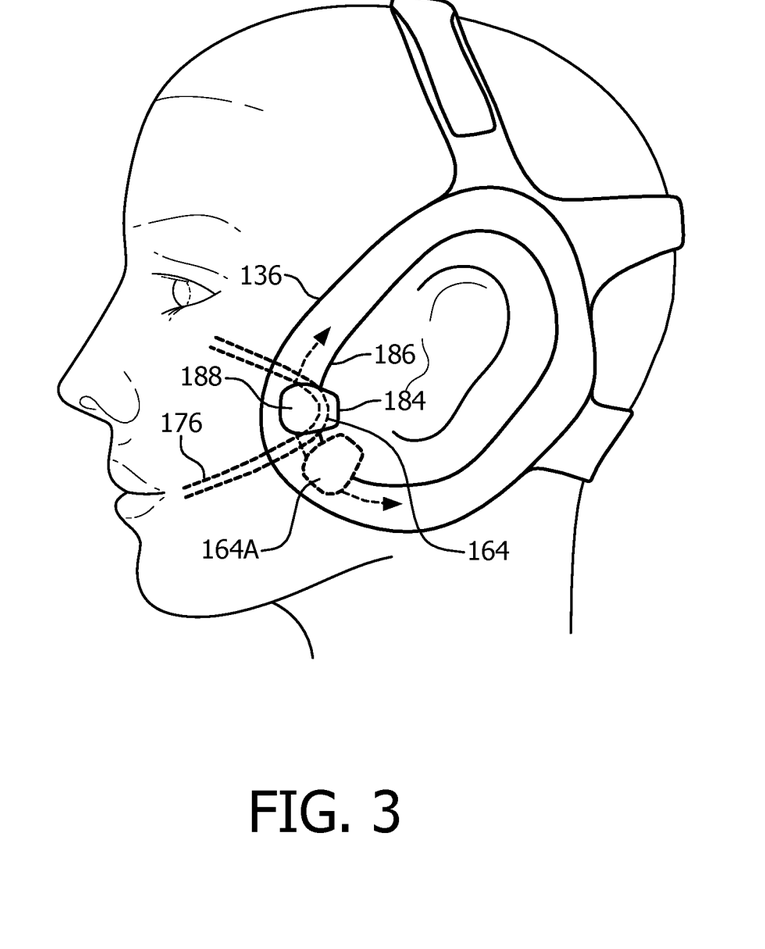
FIG. 3 is side elevational view of a headgear of the patient interface assembly of FIG. 2 and depicting a connector of a support of the patient interface assembly of FIG. 2 being movably situated on the headgear.

It is also noted that a pair of anterior struts 136 that extend in an anterior direction from a pair of temporal elements 132 have a pair of connectors 164 that are movably mounted thereon. That is, while the pair of connectors 64 of breathing apparatus 4 were affixed to the pair of anterior struts 36, it is noted that connectors 164 are advantageously movably disposed on anterior struts 136, as is illustrated in FIG. 3. The movability of connectors 164 on anterior struts 136 provides a pair of anchor points 178 that are situated anterior of the ears of the patient and that are self-adjusting to an even greater extent than in patient interface assembly 4 since the positions of anchor points 178 are themselves movable. That is, anchor points 78 of patient interface assembly 4 were generally dictated by the position at which connectors 64 were affixed to anterior struts 36 of headgear 8. However, because connectors 164 of patient interface assembly 104 are actually movably situated on anterior struts 136, anchor points 178 can themselves move along anterior struts 136, which provides even greater variability of the fit of patient interface assembly 104 to the patient, which improves comfort.

Optionally, connectors 164 can additionally be lockable or affixable in particular positions on anterior struts 136. That is, in scenario discussed above, connectors 164 can be freely floating on anterior struts 136 in order to help achieve equilibrium. This could be referred to as "passive" positioning of connectors 164. Optionally, however, connectors 164 can be configured to stay or to be retained in particular positions on anterior struts 136 as may be desired by the patient. This could be referred to as "active" positioning of connectors 164.

For example, connectors 164 may be configured to have friction between them and anterior struts 136, and such friction can be configured to be relatively high, or at least higher than the friction between connectors 164 and anterior struts 136 that could typically be overcome in the normal course during use of patient interface assembly 104 and the achievement of equilibrium of tension in strap member 168. However, connectors 164 could be manually moved by the patient along anterior struts 136 until desired positions are reached, after which connectors 164 would remain in the desired positions. That is, the friction between connectors 164 and anterior struts 136 may be sufficiently great that connectors could not be considered "freely floating" on anterior struts 136, but the patient could easily overcome such friction to manually move connectors 164 to the desired positions. Thus, while connectors 164 would be movably disposed on anterior struts 136, they would optionally not be freely floating thereon, and rather would be lockable in desired positions, whether being automatically lockable due to friction, or being manually lockable through the use of a locking mechanism that is released to allow movement but that is refastened to retain connectors 164 in the desired positions.

It is also noted that a support 116 of patient interface assembly 104 includes both an upper tension loop 180 and a lower tension loop 182. While a strap member 168 of support 116 is an individual, i.e., single cord member that is flexible and may be at least partially elastic, as is strap member 68 of breathing apparatus 4, upper and lower tension loops 180 and 182 provide enhanced adjustment of the tension in strap member 168 since it provides for separate fine tuning of the tension in the upper and lower portions of strap member 168. That is, while a strap apparatus 160 that includes connectors 164 and strap member 168 will ultimately reach a point of equilibrium of the tension within strap member 168 because each strap segment 176 is movably situated on its corresponding connector 164, and also because connectors 164 are movably situated are situated on anterior struts 136, it is noted that such equilibrium can be more quickly achieved since upper and lower tension loops 180 and 182 permit separate adjustment of tension in the upper and lower portions of strap segments 176. By permitting such fine tuning of the tensions in the upper and lower portions of the pair of strap segments 176, equilibrium of the tensions in the upper and lower portions of each strap segment 176 can be accomplished with relatively less movement of strap segments 176 with respect to connectors 164, which speeds the reaching of equilibrium and promotes comfort to the patient.

It is also noted that a pair of upper braces 148 and a pair of lower braces 152 of patient interface device 112 are in the form of channels rather than being in the form of tunnels as were upper and lower braces 48 and 52 of patient interface assembly 4. Again, the different configuration of upper and lower braces 148 and 152 tends to demonstrate that virtually any type of patient interface device 112 can be employed in conjunction with support 116 to achieve the advantageous breathing apparatus described herein.

As can be understood from FIG. 3, connectors 164 are movably situated on anterior struts 136. More particularly, each connector 164 can be seen as including a base 184 that is slidably disposed on an edge 186 of anterior struts 136. Each connector 164 further includes a pair of plates 188 that are slidably disposed on the opposite faces of anterior struts 136 adjacent edge 186. While strap apparatus 160 includes a pair of tabs 172 that are depicted in FIG. 2 as being situated adjacent connectors 164, tabs 172 are not depicted in FIG. 3 for purposes of simplicity of disclosure.

The movability of connectors 164 on anterior struts 136 is illustrated through the depiction of a connector 164A in dashed lines at an alternate position on anterior strut 136 of FIG. 3. While the position of connector 164A is likely exaggerated in view of the position of the nose and mouth of the patient, it is intended merely to demonstrate the movability of connectors 164 on anterior struts 136 and the corresponding movability of anchor points 178 of patient interface assembly 104. By enabling such variable positioning of anchor points 178, comfort is increased as is the reliability of the positioning of patient interface device 112 on the patient.

Figure 4:
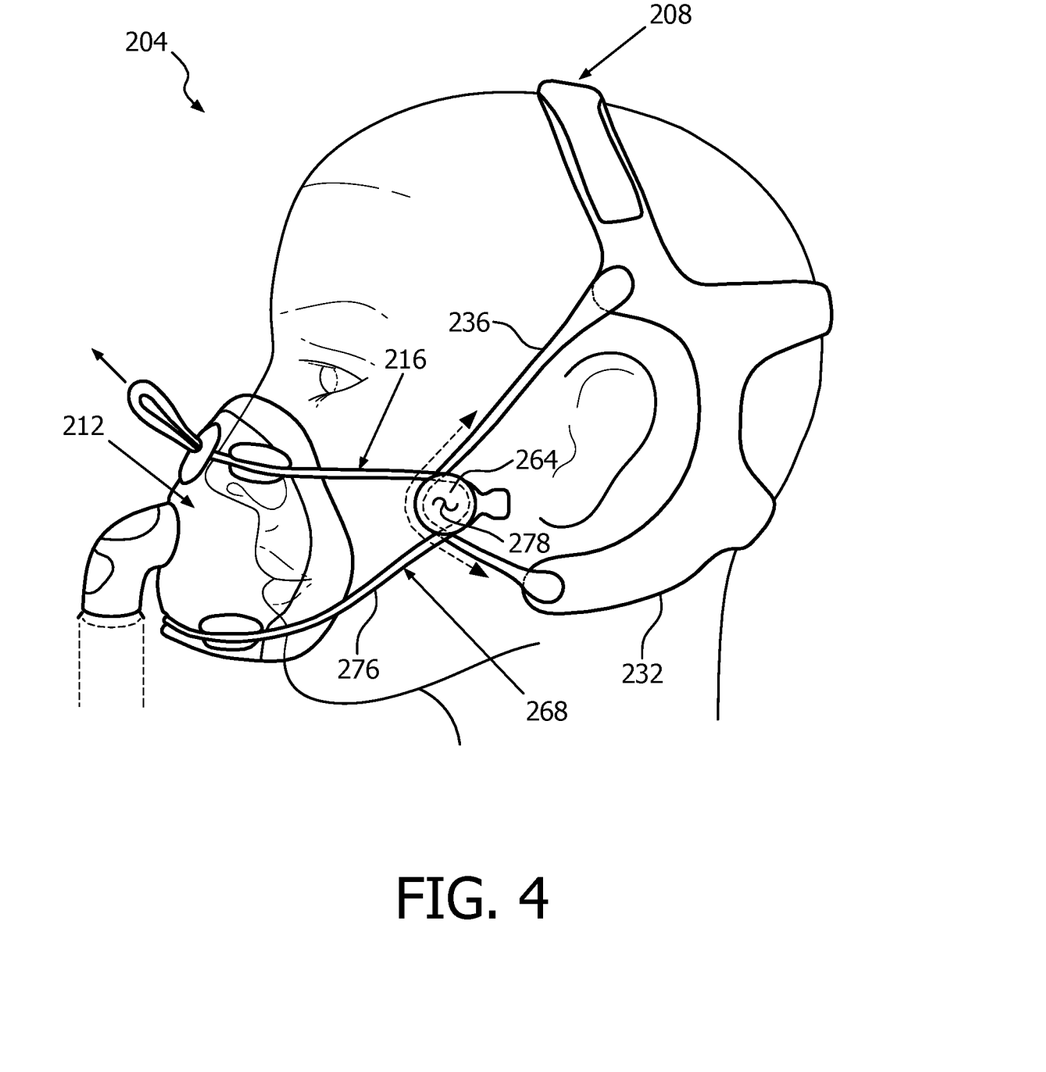
FIG. 4 is side elevational view of a patient interface assembly in accordance with a third embodiment of the present invention.

An improved patient interface assembly 204 in accordance with a third embodiment of the present invention is depicted generally in FIG. 4. Patient interface assembly 204 includes certain elements of patient interface assembly 4 and patient interface assembly 104, but provides a different exemplary combination of desirable elements. Patient interface assembly 204 includes a headgear 208, a patient interface device 212, and a support 216 that extends between headgear 208 and patient interface device 212. Support 216 includes a strap apparatus that is similar to the strap apparatus 160. It is particularly noted that headgear 208 includes a pair of flexible anterior strap elements 236 in place of the anterior struts 36 and 136. Anterior strap elements 236 extend generally in an anterior direction from a pair of temporal elements 232 of headgear 208.

While a pair of connectors 264 of support 216 are movably disposed on anterior strap elements 236, it can be seen that anterior strap elements 236 being of a flexible nature result in an even greater degree of variability of the resultant movability of anchor points 278. A strap member 268 having a pair of strap segments 276 is movably disposed on the pair of connectors 264, and connectors 264 are themselves movably disposed on anterior strap elements 236, which are themselves flexible. Such enhanced variability of positioning of anchor points 278 promotes patient comfort and enhances the ability of patient interface device 212 to be reliably maintained on the patient.

Figure 5:
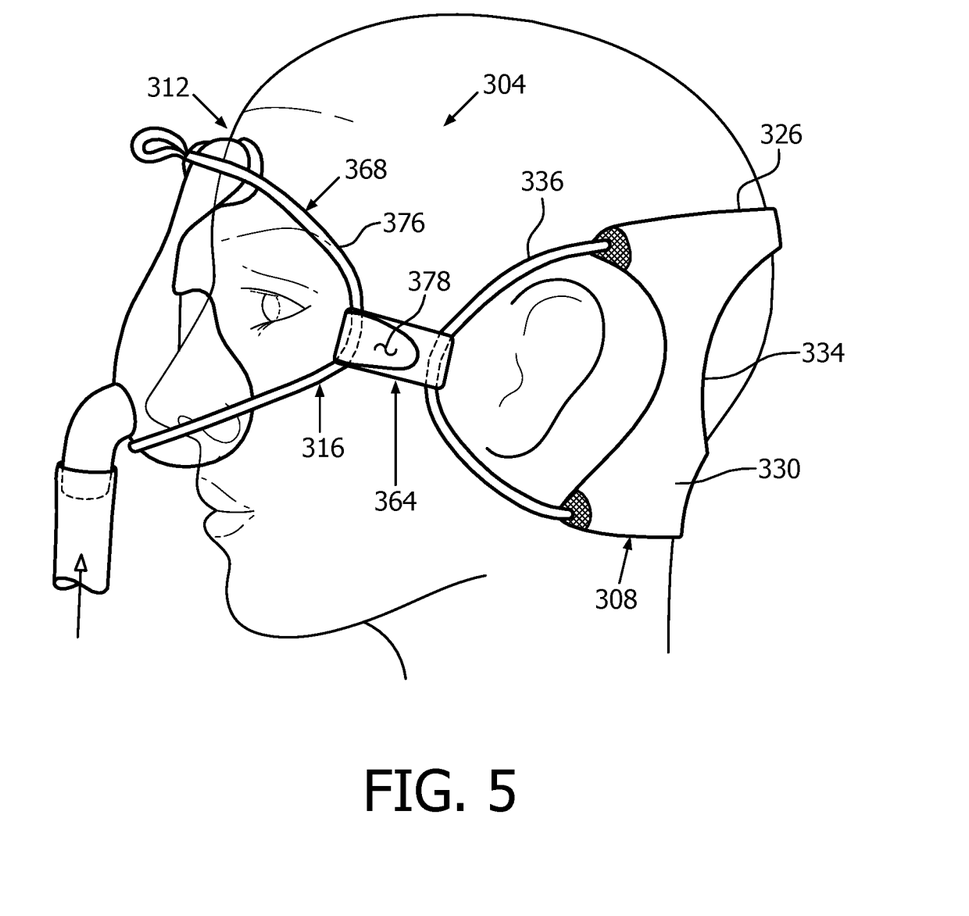
FIG. 5 is a side elevational view of a patient interface assembly in accordance with a fourth embodiment of the present invention.

An improved patient interface assembly 304 in accordance with a fourth embodiment of the present invention is depicted generally in FIG. 5. Patient interface assembly 304 includes a headgear 308, a patient interface device 312, and a support 316 that extends between headgear 308 and patient interface device 312. Support 316 includes a strap apparatus that is similar to the strap apparatus 160. The exemplary patient interface device 312 is depicted in FIG. 5 as being one that provides a flow of breathing gases to the nose only and that further includes a point of connection with the patient's forehead, which further illustrates that virtually any type of patient interface can be employed with the support variously described herein to provide the resultant advantageous breathing apparatus variously described herein.

Headgear 308 includes an upper element 326 and a lower element 330, both of which extend across the occipital region of the patient's head. A pair of junction elements 334 of headgear 308 each extend between upper and lower elements 326 and 330 on opposite sides of headgear 308. Headgear 308 further includes a pair of anterior strap elements 336 that extend in an anterior direction on opposite sides of headgear 308 from upper and lower elements 326 and 330. Again, the different configuration of headgear 308 tends to illustrate how virtually any type of headgear can be employed in conjunction with the improved support variously described herein to form the resultant improved breathing apparatus variously described herein.

Support 316 includes a unitary strap member 368 that can be said to include a pair of strap segments 376 that extend from opposite sides of patient interface device 312. Support 316 can also be said to include a pair of flexible connectors 364 that each flexibly and length-adjustably extend between one of the pair of anterior strap elements 336 and one of the pair of strap segments 376. Connectors 364 can be advantageously situated virtually anywhere along the length of anterior strap elements 336 and strap segments 376, which provides a high degree of variability of the resultant anchor points 378 that are situated anterior to the ears of the patient.

Moreover, because the pair of connectors 364 in the exemplary embodiment are formed of a flexible fabric and thus are also length adjustable, the distance between anterior strap elements 336 and strap segments 376 can further be varied to provide even greater variability of the positioning of anchor points 378. Connectors 364 can be of any of a variety of configurations but, in the present exemplary embodiment, are formed to include hook and loop fasteners or other such fasteners that permit connectors 364 to be length-adjustable. Such enhanced variability of anchor points 378 permits even greater levels of comfort for the patient and reliability of connection of patient interface device 312 with the patient.

Advantageously, therefore, the various patient interface assemblies 4, 104, 204, and 304 each provide anchor points 78, 178, 278, and 378 that are situated anterior to the ears of the patient, and each anchor point 78, 178, 278, and 378 has two connections with the corresponding patient interface device 12, 112, 212, and 312 as is indicated in FIGS. 1-2 and 4-5. Such a configuration enables comfortable yet reliable retention of patient interface device 12, 112, 212, and 312 on the patient regardless of the particular facial structures of the patient, which is advantageous. An equilibrium in the tension of strap members 68, 168, 268, and 368 is reachable by providing a movable connection between such strap members and the corresponding connectors 64, 164, 264, and 364. Additionally, connectors 164, 264, and 364 are movably disposed on headgear 108, 208, and 308, which provides even greater degrees of comfort to the patient and reliability of the connection between patient interface device 112, 212, and 312 and the patient. Further advantages will be apparent to those skilled in the art.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface assembly structured to provide a flow of breathing gases to a patient, the patient interface assembly being structured to be connected with a supply line that is structured to provide the flow of breathing gases to the patient interface assembly, the patient interface assembly comprising:

a headgear structured to extend across at least one of an occipital region and a parietal region of the patient's head;

a patient interface device structured to supply a flow of breathing gases to a mouth or a nose or both of the patient, the patient interface device comprising a mask and further comprising a fluid connection situated on the mask and structured to be connected with the supply line, the patient interface device further comprising a pair of upper braces situated on the mask and a pair of lower braces situated on the mask, the pair of upper braces and the pair of lower braces each being spaced apart from one another; and a support extending between the headgear and the patient interface device, the support comprising a strap apparatus that is unitary and a pair of tabs, a first portion of the strap apparatus extending through the pair of upper braces and extending along a location above the fluid connection, a second portion of the strap apparatus extending through the pair of lower braces and extending along another location below the fluid connection, the strap apparatus comprising a pair of flexible strap segments that extend from opposite sides of the patient interface device, one strap segment of the pair of strap segments extending from one upper brace of the pair of upper braces and one lower brace of the pair of lower braces, one tab of the pair of tabs being connected with the one strap segment, the other strap segment of the pair of strap segments extending from the other upper brace of the pair of upper braces and the other lower brace of the pair of lower braces, the other tab of the pair of tabs being connected with the other strap segment; and wherein the headgear comprises a pair of flexible strap elements that are disposed on opposite sides of the headgear and at least a portion of which are structured to extend anterior to the ears of the patient, the pair of tabs being structured to be grasped by the patient to cause the pair of strap segments to be moved in a posterior direction to cause the pair of strap segments to become connected with the pair of strap elements; and the support further comprising a pair of connectors situated on the headgear, the pair of strap segments being engaged with the pair of connectors during installation of the mask on the patient, each strap segment of the pair of strap segments having an upper portion and a lower portion and being movably disposed on a connector of the pair of connectors to enable tension in the upper and lower portions to reach an equilibrium.

2. The patient interface assembly of claim 1, wherein the pair of connectors are each additionally lockable in a particular position on the headgear.

3. The patient interface assembly of claim 1, wherein the pair of strap segments are movable with respect to the pair of upper braces and the pair of lower braces.

4. The patient interface assembly of claim 3, wherein the strap apparatus further comprises at least a first adjustment element structured to adjust the tension in the strap apparatus.

5. The patient interface assembly of claim 4, wherein the at least first adjustment element is disposed on the patient interface device.

6. The patient interface assembly of claim 5, wherein each strap segment extends from a first location, with one first location situated at each side of the patient interface device, and wherein the at least first adjustment element is disposed generally between the first locations.

7. The patient interface assembly of claim 1, wherein the fluid connection is situated at a central location on the mask.

8. The patient interface assembly of claim 1, wherein the mask is structured to cover the mouth and the nose of the patient.

9. The patient interface assembly of claim 1, wherein the pair of upper braces and the pair of lower braces are in the form of tunnels in which the pair of strap segments are received.

10. The patient interface assembly of claim 9, wherein the pair of strap segments are movable with respect to the pair of upper braces and the pair of lower braces.

11. The patient interface assembly of claim 1, wherein the headgear comprises a pair of anterior struts, the pair of connectors being movably situated on the pair of anterior struts.

* * * * *